(12) United States Patent
Fujimura et al.

(10) Patent No.: US 7,306,941 B2
(45) Date of Patent: Dec. 11, 2007

(54) BIOCHEMICAL MEASURING CHIP AND MEASURING APPARATUS

(75) Inventors: Toru Fujimura, Asaka (JP); Yasushi Goto, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 451 days.

(21) Appl. No.: 11/007,366

(22) Filed: Dec. 9, 2004

(65) Prior Publication Data

US 2005/0250198 A1 Nov. 10, 2005

(30) Foreign Application Priority Data

May 6, 2004 (JP) ............................. 2004-136990

(51) Int. Cl.
*C12M 1/34* (2006.01)
*C12M 3/00* (2006.01)

(52) U.S. Cl. .................. 435/288.3; 436/518; 436/524; 436/527; 435/7.1; 435/283.1; 435/287.1; 435/287.2; 435/288.7; 422/50; 422/61; 422/68.1; 422/82.05; 422/82.09; 359/577; 359/580; 359/586; 359/589

(58) Field of Classification Search ................ 436/518, 436/524, 527; 435/7.1, 283.1, 287.1, 287.2, 435/287.9, 288.3, 288.7; 422/50, 61, 68.1, 422/82.05, 82.09; 359/577, 580, 586, 589
See application file for complete search history.

(56) References Cited

U.S. PATENT DOCUMENTS

| | | | | |
|---|---|---|---|---|
| 4,558,012 A | | 12/1985 | Nygren et al. | |
| 4,820,649 A | * | 4/1989 | Kawaguchi et al. | 436/501 |
| 4,822,566 A | * | 4/1989 | Newman | 422/82.01 |
| 5,418,136 A | * | 5/1995 | Miller et al. | 435/5 |
| 5,468,606 A | * | 11/1995 | Bogart et al. | 435/5 |

(Continued)

FOREIGN PATENT DOCUMENTS

JP    2004-132799    10/2002

(Continued)

OTHER PUBLICATIONS

Jenison, R., et al., "Inteference-based detection of nucleic acid targets on optically coated silicon", Nature Biotechnology Vo. 19, Jan. 2001, pp. 62-65.

(Continued)

*Primary Examiner*—Long V. Le
*Assistant Examiner*—Melanie J. Yu
(74) *Attorney, Agent, or Firm*—Reed Smith LLP; Stanley P. Fisher, Esq.; Juan Carlos A. Marquez, Esq.

(57) ABSTRACT

A simple and convenient sensor and measuring apparatus utilizing the optical interference effect of an optical thin film capable of measuring the binding between biochemical substances at a high throughput and having alkali resistance. An optical thin film of silicon nitride is disposed on the first surface and the rear surface of a silicon substrate, and the thickness of the silicon nitride film is modified in a direction parallel to the film. A portion of the thin film with increased thickness is used as a sensor upon which a probe is disposed, and over which a sample-containing solution is caused to flow. The binding between the probe and biochemical sample is detected based upon the change of the intensity of reflected light.

14 Claims, 18 Drawing Sheets

U.S. PATENT DOCUMENTS

| | | | | |
|---|---|---|---|---|
| 5,482,830 | A * | 1/1996 | Bogart et al. | 435/5 |
| 5,494,829 | A * | 2/1996 | Sandstrom et al. | 436/518 |
| 5,541,057 | A * | 7/1996 | Bogart et al. | 435/5 |
| 5,550,063 | A * | 8/1996 | Bogart | 436/518 |
| 5,552,272 | A * | 9/1996 | Bogart | 435/6 |
| 5,629,214 | A * | 5/1997 | Crosby | 436/518 |
| 5,631,171 | A * | 5/1997 | Sandstrom et al. | 436/518 |
| 5,639,671 | A * | 6/1997 | Bogart et al. | 436/518 |
| 5,869,272 | A * | 2/1999 | Bogart et al. | 435/7.32 |
| 6,933,112 | B1 * | 8/2005 | Drewes et al. | 435/6 |
| 2004/0070764 | A1 | 4/2004 | Fujimura | |
| 2007/0063304 | A1 * | 3/2007 | Matsumoto et al. | 257/462 |

FOREIGN PATENT DOCUMENTS

| | | |
|---|---|---|
| WO | WO 94/03774 | 6/1993 |
| WO | WO 2004/031760 A1 | 8/2003 |

OTHER PUBLICATIONS

Sandstrom, T., et al. "Visual detection of organic monomolecular films by interference colors", Applied Optics, vol. 24, No. 4, Feb. 15, 1985, pp. 472-479.

Poenar, D.P., et al., "Colour sensors based on active inteference filters using silicon-compatible materials", Elseiver, Sensors and Actuators, 1997, pp. 513-523.

Torbjörn Sandström et al., "Visual Detection of Organic Monomolecular Films by Inteference Colors", Applied Optics, vol. 24, No. 4 (Feb. 15, 1985), pp. 472-479.

A. Brecht et al., "Optimised Layer Systems for Immunosensors Based on the RIFS Transducer", Fresenius J. Anal. Chem (1994), pp. 360-366.

Dietmar Leipert et al., "Interaction Between Volatile Organic Compounds and Cyclopeptides Detected with Reflectometric Interference Spectroscopy", Analytica Chimica Acta, vol. 392 (1999), pp. 213-221.

* cited by examiner

FIG. 21

TABLE 1

| | SixNy<br>x ≈ 0.43<br>y ≈ 0.57<br>REFRACTIVE<br>INDEX<br>2.0 | SixNy<br>x ≈ 0.51<br>y ≈ 0.49<br>REFRACTIVE<br>INDEX<br>2.2 | SixNy<br>x ≈ 0.52<br>y ≈ 0.48<br>REFRACTIVE<br>INDEX<br>2.3 | SiO$_2$ |
|---|---|---|---|---|
| 6 HOURS | 0 Å | 0 Å | 2 Å | 28 Å |
| 24 HOURS | 1 Å | 4 Å | 5 Å | 100 Å |
| 48 HOURS | 1 Å | 7 Å | 9 Å | 191 Å |

# BIOCHEMICAL MEASURING CHIP AND MEASURING APPARATUS

CLAIM OF PRIORITY

The present application claims the benefit under 35 U.S.C. § 119 of the earlier filing date of Japanese Patent Application JP 2004-136990 which was filed on May 6, 2004, the content of which is hereby incorporated by reference into the present application.

BACKGROUND OF THE INVENTION

1. Field of the Invention

The present invention relates to a biochemical sensor utilizing an optical thin film, components for the sensor, and a measuring apparatus utilizing the same.

2. Description of the Background

The bindings between biochemical substances, such as in an antigen-antibody reaction, have generally been measured using a "label" such as a radioactive substance or fluorescence materials. Labeling is laborious and, particularly, the labeling of proteins is sometimes complicated in view of the method and the fact that the proteins may be altered by this labeling process. In view of the above, a biochemical sensor utilizing the change of interference color of an optical thin film has been known as a method of directly measuring the binding between biochemical substances in a simple and convenient manner, without using a label.

A biochemical sensor is described in the article of T. Sandstrom, et. al., APPL. OPT., 24, 472, 1985 (hereafter "Non-Patent Document 1"). An example is to be described with reference to the model shown in FIG. 1. An optical thin film 2 is disposed on a substrate 1. The refractive index of air is 1.00, the refractive index of the material for the optical thin film 2 is 1.50, and the refractive index of the substrate 1 is 2.25 in this exemplary sensor. When the thickness of the optical thin film is adjusted or controlled to an optical length corresponding to ¼ (or an odd number multiple thereof) of a wavelength $\lambda_0$ of visible light (for example, ¾ $\lambda_0$, 5/4$\lambda_0$, etc.), the optical thin film acts as an anti-reflection film in which the intensity of reflected light perpendicular to the optical thin film is 0 at a wavelength $\lambda_0$ as shown by a reflection spectrum A in FIG. 2. Thus, the sensor produces an interference color.

A single molecular layer of a first biochemical substance 3 is disposed on the optical thin film 2. Assuming the biochemical substance as a protein, the refractive index is about 1.5 and the thickness of the layer is about 10 nm. This means that the thickness of the optical thin film increases in terms of optics. Therefore, the reflection spectrum changes from a solid line A to a short dashed line A' in FIG. 2, and the interference color changes. When a second biochemical substance 4 is biochemically binded to the first biochemical substance 3, the film thickness further increases which causes a change from the short dashed line A' to the broken line A" in FIG. 2 and another change in the interference color. Thus, binding of the second biochemical substance 4 may be detected.

As a general detection procedure, the optical thin film 2 on the substrate 1 covered with a single molecular layer 3 of a first biochemical substance is prepared first. This preparation is put into a solution of a second biochemical substance (4). Then, the preparation is taken out of the solution, dried and then the change of the interference color from the short dashed line A' to broken line A" in FIG. 2 is examined.

Further, light reflection caused at the back of the substrate 1 may be suppressed by using a light absorbing material, for example silicon, as the material for the substrate 1. Silicon monoxide is vapor deposited as an optical thin film to the silicon substrate and the uppermost surface layer is formed into silicon dioxide of 2 to 3 nm thickness obtained by spontaneous oxidation of silicon monoxide, thereby preparing a chemically stable film.

As described above, in the existing biochemical sensors utilizing an optical thin film disposed on the light absorbing substrate, the interference color is measured after taking the sensor out of solution and drying the sensor in air. Further, Japanese Patent Application JP-A No. 195242/1983 (hereafter "Patent Document 1") describes detection of a chemical substance using dielectric layers. Patent Document 1 describes that a $SiO_2$ layer is disposed on the surface of a carrier comprised of silicon to form a reflection-reducing coating.

However, since the sensor described in Non-Patent Document 1 above is taken out in the air and the interference color is measured after drying for detection, it takes an undesirable amount of time during the drying step, and improvement for the throughput is desired. Further, since measurement is conducted after a lapse of a predetermined time after the beginning of the reaction, the sensor is sometimes taken out into the air before saturation of the reaction, depending upon the way in which the predetermined time is set, so that measurement cannot always be conducted with high (maximum) accuracy. On the other hand, if a long predetermined time is set in order for measurement to be taken after sufficient saturation of the reaction, because the sensor is dipped into the solution after waiting for the saturation of the reaction, the efficiency is poor in view of time.

At the same time, with respect to the chemical resistance of the sensor, an alkali cleaning is an effective method for removing organic matters that may be deposited on the sensor. Further, when surface modification is applied for immobilization of the first biochemical substance on the sensor surface and for preventing non-specific adsorption of molecules to the sensor surface, a sensor chip is sometimes dipped in an alkali solution, so that alkali resistance is important. However, a silicon substrate has poor resistance to an aqueous alkali solution, and it dissolves in an aqueous 1 M sodium hydroxide while evolving bubbles. Further, using silicon dioxide as the uppermost layer of the optical thin film described in Non-Patent Document 1 has no sufficient resistance to alkali.

SUMMARY OF THE INVENTION

It is an object of the present invention to provide a simple and convenient biochemical sensor comprised of an optical thin film on a light absorbing substrate which utilizes the effect of light interference. The sensors of the present invention include good resistance to alkali and are capable of measuring the binding between biochemical substances at a high throughput, when compared to existing sesnors.

In accordance with the present invention, the foregoing object can be attained by the following constitution.

(1) In a sensor chip comprised of an alkali-resistant optical thin film formed on a light absorbing substrate and a probe formed on the surface of the optical thin film, a solution containing a sample that interacts with the probe is supplied. The intensity of reflected light that changes before and after the interaction is detected in a state where the solution is supplied. As the optical thin film, silicon nitride, tantalum oxide or similar materials having an alkali resistance are preferably used.

Further, a protective film comprising an alkali resistant material such as silicon nitride or tantalum oxide is disposed to the surface of the substrate having the sensor at a region other than that for the sensor, and on the back surface (i.e., rear surface) of the substrate. This can provide the surface of the substrate having the sensor and the rear surface thereof with alkali resistance of the chip. Further, the optical path length of the film is made different for the surface having the sensor between the sensor portion and a mark or a character showing the sensor portion and other portions such that they exhibit different colors.

In the present invention, binding between the biochemical substances is detected mainly by utilizing the change of the interference color of the optical thin film in a solution. In this description, a "biochemical substance" is a substance that biochemically binds with another substance and includes not only substances produced in-vivo such as proteins, nucleic acids, lipides and saccharides, but also external substances binding with in-vivo molecules such as chemical substances and endocrine-disrupting chemicals.

(2) The refractive index of the optical thin film is controlled so as to obtain a distinct interference color in the aqueous solution. For example, the refractive index of the optical thin film on the silicon substrate may be controlled to 2.2. Alternatively, a plurality of layers with different refractive indexes may be combined as the optical thin film. For example, for the optical thin film of the silicon substrate, a film with a refractive index of 2.4 is formed on a substrate and a film with a refractive index of 2.0 is formed thereon.

Alternatively, a gradient-index layer having a refractive index of 2.0 on the surface of the sensor and having a higher refractive index at the boundary with the substrate may be used as the optical thin film. In this case, the refractive index of the optical thin film is changed continuously within a range from 2.0 to 2.6 in the direction of the film thickness. For example, the refractive index is changed continuously for the optical thin film on the silicon substrate such that the refractive index is 2.4 at the boundary with the substrate and the refractive index is 2.0 at the sensor surface of the optical thin film. The film with the refractive index of 2.0 is a film having a highest alkali resistance in silicon nitride and a chemically stable sensor is obtained by using the film for the uppermost layer. Further, the refractive index for silicon nitride can be changed from 2.0 to 2.6 by changing the mixing ratio of gases by a CVD method.

(3) Detection can be attained by a detection apparatus having optical fibers for irradiating light on each of a plurality of kinds of probes and for detecting reflected light, along with a measuring instrument for measuring the change of the intensity of the reflected light. In this case, since optical fibers are provided on each type of probe, a plurality of kinds of reactions can be detected at approximately the same time. Then, when a chip holding portion is provided for holding the sensor chip, and the sensors and the optical fibers are arranged asymmetrically with respect to the direction of rotation relative to the chip holding portion, error can be detected by a detection device by attaching the sensor chip to the chip holding portion in an erroneous direction.

An example of the chip is comprised of a silicon substrate, a first silicon nitride film disposed on the surface of the silicon substrate, and a second silicon nitride film disposed at the rear surface of the silicon substrate, in which the first silicon nitride film has a first region for immobilizing a probe that binds with a biochemical substance at the surface. Further, the refractive index of the first silicon nitride film may have a value with a range from about 2.0 to about 2.6, and the probe may be formed of a protein. Further, the first silicon nitride film may comprise a third silicon nitride film disposed to the surface of the silicon substrate and having a refractive index of about 2.4, and a fourth silicon nitride film disposed to the surface of the third silicon nitride film may have a refractive index of about 2.0.

Each of the first and second silicon nitride films may have a refractive index of about 2.4 at the surface in contact with the silicon substrate and a refractive index of about 2.0 at the opposite surface, respectively. The refractive index of the films may be changed continuously from the surface in contact with the silicon substrate to the other surface. Further, each of the first and second silicon nitride films may have a refractive index that changes exponentially from the film surface to the surface of the silicon substrate.

According to the present invention, the binding of a biochemical substance can be measured at a high throughput using a semiconductor chip capable of applying alkali cleaning and surface modification using an alkali, as described in more detail below.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein:

FIG. 21 shows Table 1 detailing the results of an alkali resistance test.

DETAILED DESCRIPTION OF THE INVENTION

First Exemplary Embodiment "Example 1"

Figure 1:
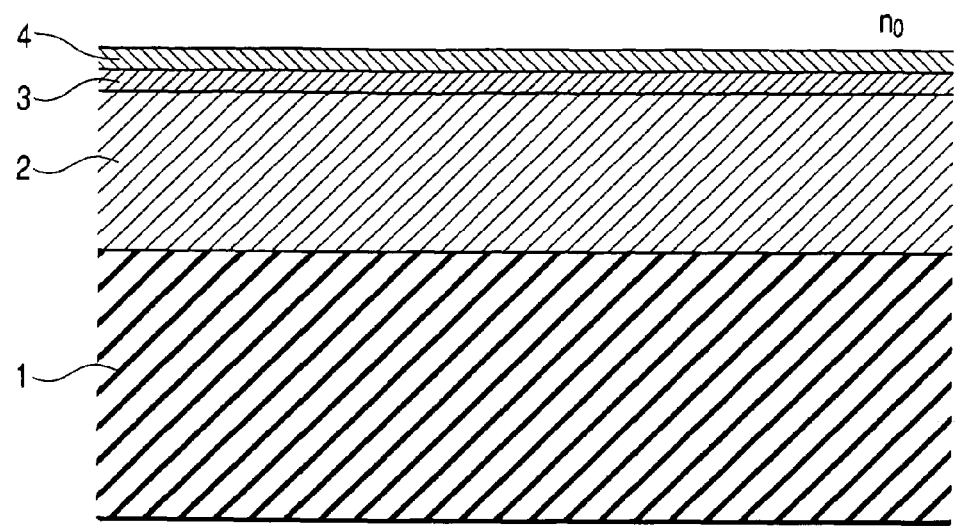
FIG. 1 shows the constitution of a biochemical sensor.
Figure 2:
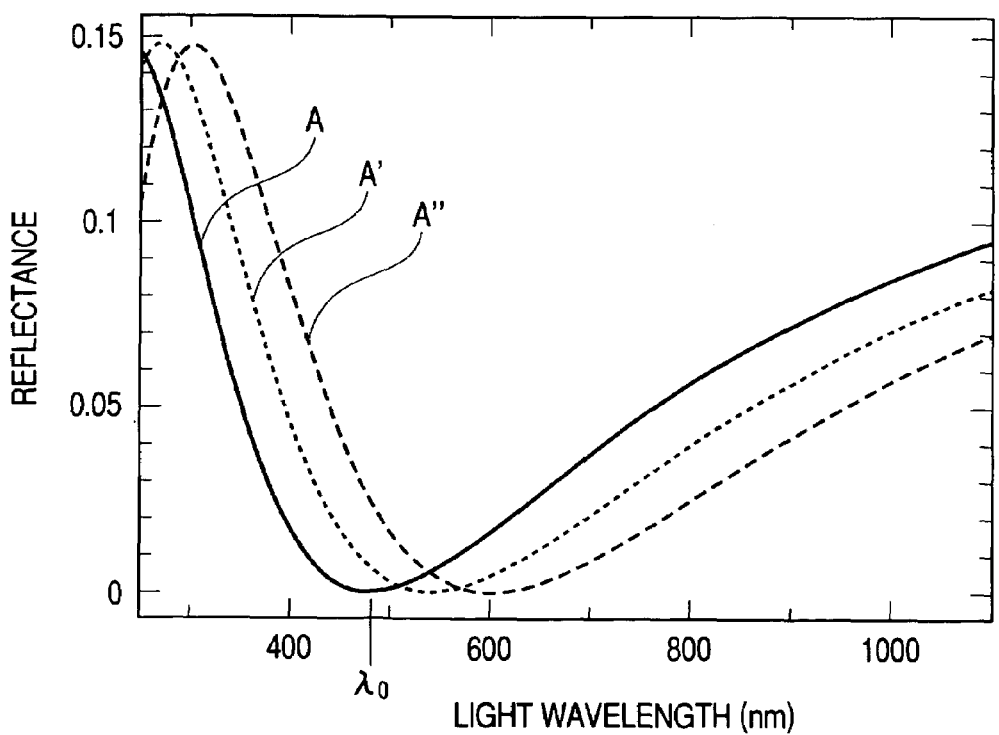
FIG. 2 shows the change of interference color of a biochemical sensor.
Figure 3A:
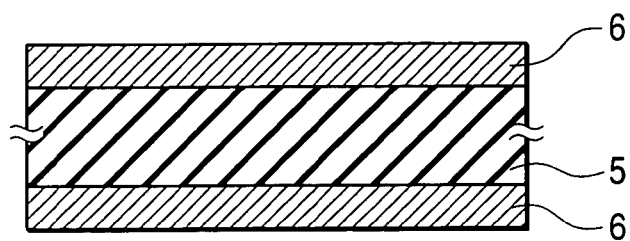
FIG. 3 shows the manufacturing steps for a biochemical sensor, including four successive sub-steps (FIG. 3A, FIG. 3B, FIG. 3C, and FIG. 3D)
Figure 3B:
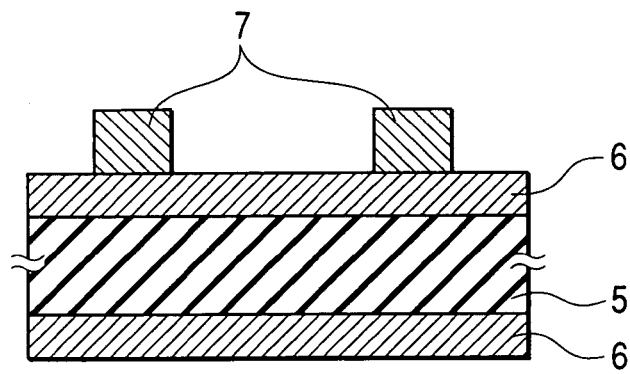

A method of manufacturing a biochemical sensor chip having an alkali resistance will now be described. In the following description, the term "about" with respect to the value for the refractive index means a range within ±0.5 for the indicated value. FIG. 3A and FIG. 3B show an example of a method of manufacturing a sensor according the present invention. As shown in FIG. 3A, an optical thin film 6 of silicon nitride ($Si_xN_y$, refractive index: 2.2) of about 70 nm thickness is formed to the surface and the rear surface (the lower portion in FIG. 3A) of a silicon substrate 5 having a substantially planar surface using a chemical vapor deposition method (CVD).

Figure 4:
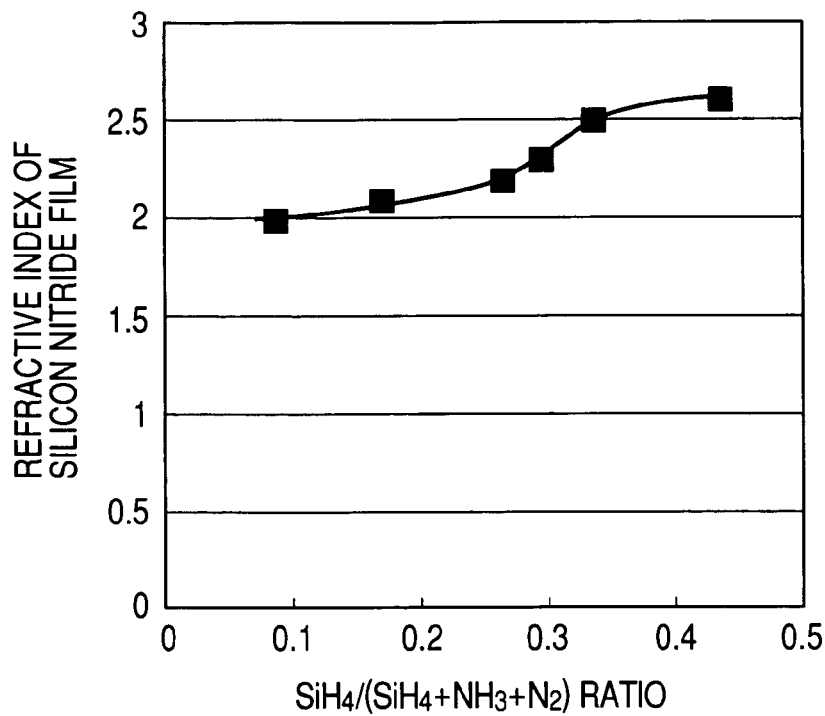
FIG. 4 is a graph showing the refractive index of an optical thin film in a biochemical sensor according to the present invention.

Usually, the silicon nitride film has a composition comprising 4 nitrogen relative to 3 silicon at which the refractive index is 2. The refractive index can be controlled within a range from 2.0 to 2.6 by controlling the film deposition condition for the silicon nitride film. FIG. 4 shows the refractive index of silicon nitride films to be formed based on a mixing ratio of monosilane in a mixed gas of monosilane, ammonia and nitrogen used for the CVD method. Specifically, the refractive index of the silicon nitride film can be controlled within a range from about 2.0 to about 2.6 by controlling the mixing ratio of the monosilane in monosilane, ammonia and nitrogen from about 0.07 to about 0.45 in the starting gas mixture. However, it is estimated that as the ratio of monosilane in the starting gas mixture increases, the value for "silicon/nitrogen" becomes more than ¾ in the silicon nitride film composition.

Specifically, the compositional ratio of a film with a refractive index of 2.0 is nitrogen 4: silicon 3. That is, nitrogen is about 0.57 based on about 0.43 of silicon. In a film with a refractive index of 2.2, nitrogen is about 0.49 based on about 0.51 of silicon in the compositional ratio. In a film with a refractive index of 2.3, nitrogen is about 0.48 based on about 0.52 of silicon in the compositional ratio. As described above, a film of higher refractive index has a higher silicon ratio in the compositional ratio.

Figure 3C:
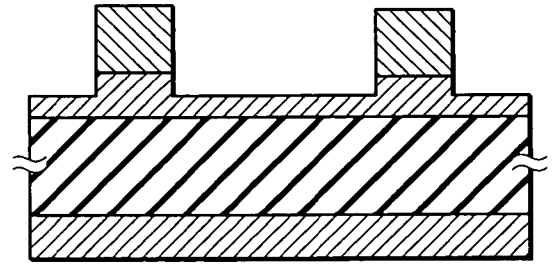
Figure 3D:
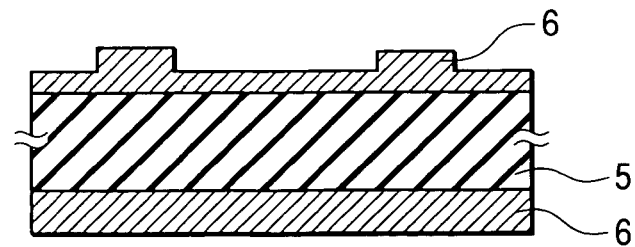

Continuing with the manufacturing method, as shown in FIG. 3B, a resist is coated, exposed and developed by photolithography to form a resist pattern 7 to a sensor portion and a portion for a mark and a character showing the sensor portion. Successively, as shown in FIG. 3C, the silicon nitride film is etched to 40 nm thereby forming a step in the silicon nitride film. Then, as shown in FIG. 3D, the resist is removed.

Figure 5:
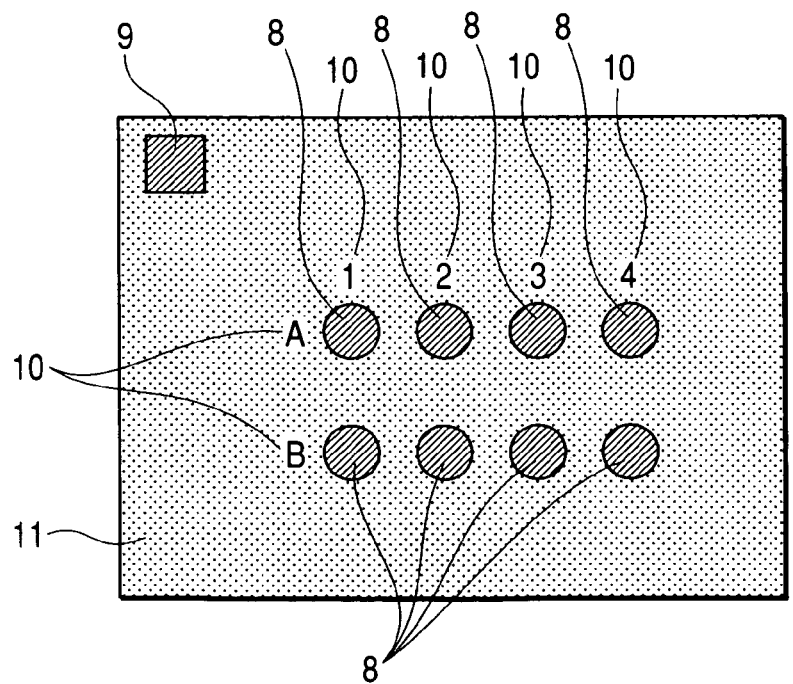
FIG. 5 is an upper plan view (top view) of a biochemical sensor according to the present invention.

FIG. 5 shows an upper plan view (top view) of the sensor chip. A sensor portion 8, a mark 9 indicating the orientation of the sensor chip, characters 10 each showing the name of the sensor portion, and a protective film 11 are disposed on the upper surface of the sensor chip. The sensor portion 8, the mark 9 indicating the direction of the sensor chip, and the characters 10 each showing the name of the sensor portion are simultaneously formed by drawing a resist pattern as shown in FIG. 3B.

The thickness of silicon nitride for the sensor portion 8, the mark 9 and the characters 10 is about 70 nm, and these portions show blue color due to the interference color thereof. The thickness of the protective layer 11 is thinned to about 30 nm by etching as shown in FIG. 3C, and it exhibits a color nearly equal with that of silicon, being slightly tinted brown, so that it can be distinguished by visual observation. That is, at least the sensor portion 8 and the protective layer 11 are different in thickness and can be distinguished further in view of colors by the naked eye. This is convenient when a solution of the first biochemical substance is dripped into each of the sensor portions in order to immobilize the first biochemical substance (probe) to each of the sensor portions.

As described above, a sensor chip with excellent alkali resistance may be obtained. Table 1 (see FIG. 21) summarizes the result of an alkali resistance test of silicon nitride and silicon dioxide. Table 1 shows the decrement of the film thickness of a silicon nitride film with refractive index 2.0, a silicon nitride film with refractive index 2.2, a silicon nitride film with refractive index 2.3, and a silicon dioxide film formed and immersed in an aqueous solution of 1 M sodium hydroxide for 6 hours, 24 hours and 48 hours respectively. The silicon nitride films of the respective refractive indexes were obtained by the CVD method described above. The silicon dioxide film was fabricated by thermally oxidizing the surface of the silicon substrate. From Table 1, it can be seen that silicon nitride has better alkali resistance compared with silicon dioxide. While the film thickness is decreased by 100 Å in 24 hours for the silicon dioxide film, that is, film is dissolved by 10 nm, the film thickness is decreased only by several Å or less in silicon nitride.

As described above, it can be seen that the silicon nitride film is excellent in alkali resistance. Particularly, the silicon nitride film of 2.0 refractive index has the best alkali resistance of the test. In a silicon nitride film with a refractive index being controlled to 2.2 or 2.3, the alkali resistance tends to be lowered compared with that of 2.0 refractive index. Since silicon itself is etched by an alkali solution such as an aqueous solution of sodium hydroxide, it is considered that those of higher silicon ratio show lower alkali resistance. It is expected that the composition x/y of the silicon nitride film ($Si_xN_y$) with a refractive index of 2.3 is about 1.1. In view of the result of the test described above, when the alkali resistance is taken into consideration, x/y for the silicon nitride film ($Si_xN_y$) at the surface of the sensor portion may be 1.1 or less, with a view point of the silicon ratio.

Materials other than silicon nitride also have identical refractive indexes and alkali resistances. As an example, resistance of a tantalum oxide film by sputter deposition (refractive index, about 2.06) to an aqueous solution of 1 M sodium hydroxide was tested. As a result, it was confirmed that the film thickness was decreased by about 6 Å after 24 hours of immersion. In the case of using the tantalum oxide film, a performance comparable with that of silicon nitride can be obtained, for example, by controlling the film quality using a CVD or similar method.

Figure 6A:
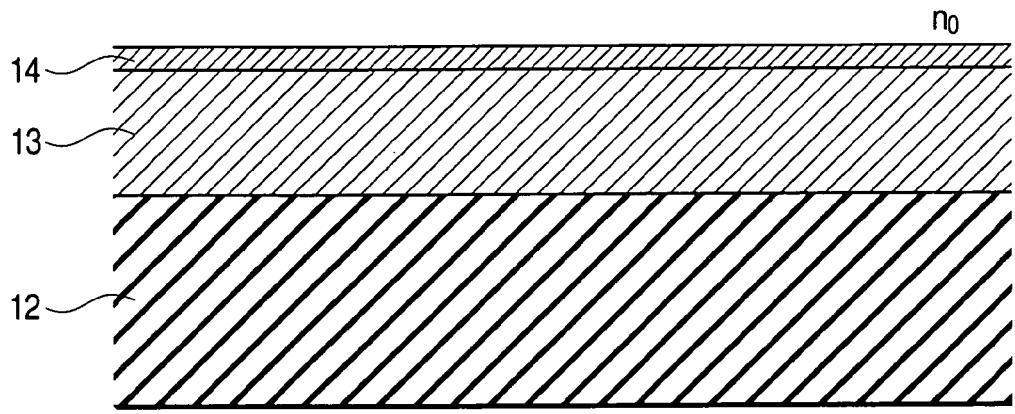
FIG. 6 details two views of the constitution of a biochemical sensor according to the present invention (FIG. 6A and FIG. 6B)
Figure 6B:
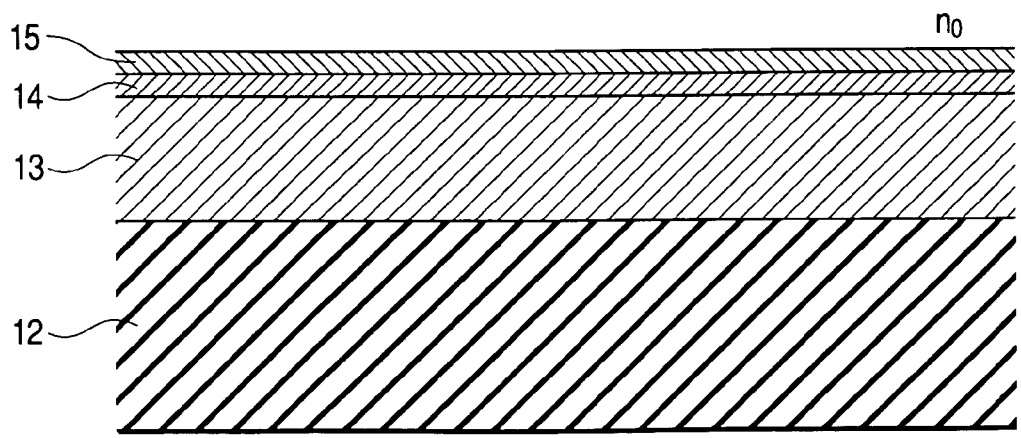

The sensor shows a distinct interference color in a solution, and the interference color changes depending on the binding of a biochemical substance. FIG. 6A and FIG. 6B show models used for computer simulation. The sensor portion is an optical thin film 13 comprising silicon nitride on a silicon substrate 12 for immobilizing the first biochemical substance (probe). Further, the optical thin film 13 had a refractive index of 2.2 and a thickness of 70 nm. In the examples described below, the sensor portion may also be silicon nitride with a controlled refractive index. The refractive index no at the background was 1.3330.

The first biochemical substance (probe) was formed as a layer 14 having a refractive index of 1.5 and a thickness of 10 nm (FIG. 6A). By supplying a sample containing a second biochemical substance to the biochemical sensor, the first biochemical substance and the second biochemical substance are binded (FIG. 6B). The second biochemical substance is shown as a layer 15 having a refractive index of 1.5 and a thickness of 10 nm.

Figure 7:
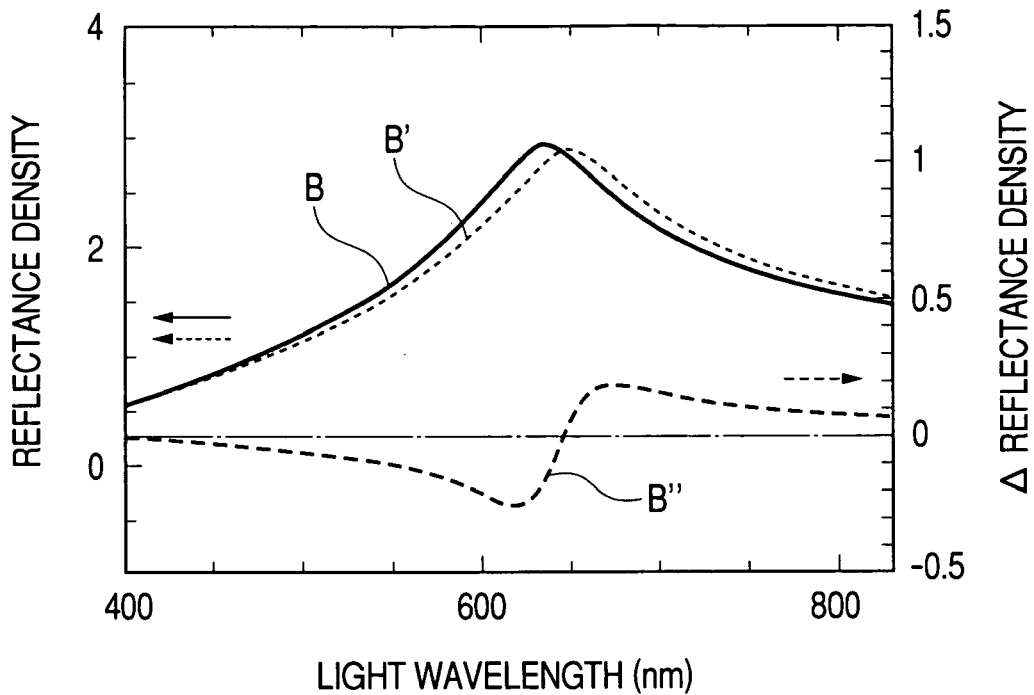
FIG. 7 is a graph showing the change of reflection spectrum before bonding and after bonding with protein.

FIG. 7 shows the reflection spectra. The reflectance density on the ordinate was $-\log_{10}R$, where R represents the reflectance of the sensor. FIG. 7 shows the reflectance density spectra at the wavelength from 400 nm to 830 nm. The graph shows the reflection spectrum of the sensor applied with the first biochemical substance layer in FIG. 6A as a solid line B and a reflection spectrum of the sensor applied with the second biochemical substance layer in FIG. 6B as a short dashed line B', respectively. From the reflection spectra shown in FIG. 7, it can be seen that the reflection decreases by the optical interference at a wavelength near 620 nm. Further, it can be seen that the spectrum shifts entirely toward a longer wavelength side by the addition of the biochemical substance layer. A broken line B" shows a differential spectrum obtained by subtracting the solid line B from the short dahsed line B'. As seen from the differential spectrum B", binding of the second biochemical substance to the first biochemical substance can be measured based on the change of the reflection spectrum of the sensor, that is, the change of the reflected light intensity.

A method of immobilizing a protein is described as an example of immobilizing the first biochemical substance to the sensor portion. At first, a sensor chip is dipped in 1 M sodium hydroxide for 24 hours to be put to alkali cleaning. Successively, plasmas of oxygen or atmospheric air are irradiated to the sensor chip. Then, a surface treatment is conducted by 3-aminopropyl trimethoxy silane to introduce amino groups on the surface of the optical thin film. Then, 2 mg of N-hydroxy succinimide, 10 mg of water soluble carbodiimide and 1 mg of protein are dissolved in 1 ml of deionized water to activate the carboxyl groups of the protein. The solution is dropped to a region in which the amino groups are introduced to immobilize the protein by way of covalent bond to the amino groups on the sensor surface. Then, the sensor chip is rinsed with deionized water and a nitrogen gas is blown for drying.

As another method of immobilizing the biochemical substance, a description is made of an immobilizing method using dextran as a linker, which is known as an immobilization method with less non-specific adsorption of molecules to the sensor surface. At first, the sensor chip is dipped in 1 M sodium hydroxide for 24 hours for alkali cleaning. Successively, plasmas of oxygen or atmospheric air are irradiated to the sensor chip. Then, a surface treatment is conducted by 3-glycidoxypropyl trimethoxy silane to introduce epoxy groups to the surface of the optical thin film. Successively, the sensor chip is dipped for 20 hours into a 0.3 g/ml of dextran solution, dissolved in an aqueous solution of 0.1 M sodium hydroxide. Dextran is bonded to the sensor surface by the procedures described above. Then, the sensor chip is dipped into 1 M bromoacetic acid solution dissolved in an aqueous solution of 2 M sodium hydroxide for 16 hours, by which carboxyl groups are introduced into dextran.

It has been confirmed that when a silicon nitride film with a refractive index controlled to 2.3 having the lowest alkali resistance among the silicon nitride examples in Table 1 (FIG. 21) is dipped in an aqueous solution of 2 M sodium hydroxide for 24 hours, the film thickness is decreased by 9 Å or less. Silicon oxide has a sufficient resistance also to an aqueous solution of 2 M sodium hydroxide when compared with a silicon oxide film. A biochemical substance having a primary amine, for example, a protein, can be bonded to dextran as a linker by activating the carboxyl groups using an aqueous solution of N-hydroxy succinimide and water soluble carbon diimide.

Second Exemplary Embodiment "Example 2"

When the alkali resistance of silicon nitride having different refractive indexes in Table 1 shown in FIG. 21 is compared, the silicon nitride film with a refractive index of 2.0 has the best resistance, and the resistance is preferred in the order of a film with a refractive index of 2.2 and a film with a refractive index of 2.3. It can be said that the resistance is improved as the compositional ratio of the silicon nitride film is nearer to the compositional ratio of nitrogen 4:silicon 3 which is the most chemically stable. This example shows a biochemical sensor chip of better alkali resistance by using an optical thin film with a refractive index of 2.0, that is, a silicon nitride film at a compositional ratio of nitrogen 4: silicon 3, on a silicon substrate instead of the optical thin film with a refractive index of 2.2 on a silicon substrate in Example 1.

The biochemical sensor chip can be obtained in the same manner and by the method of manufacturing the biochemical sensor chip in Example 1, by forming silicon nitride of about 75 nm thickness with a refractive index of 2.0 to the surface and the rear surface of the silicon substrate 5 having a substantially planar surface shown in FIG. 3A by a CVD method. This method is instead of forming an optical thin film 6 of silicon nitride ($Si_xN_y$, refractive index 2.2) of 70 nm thickness to the surface and the rear surface of the silicon substrate 5 having a substantially planar surface.

Figure 8:
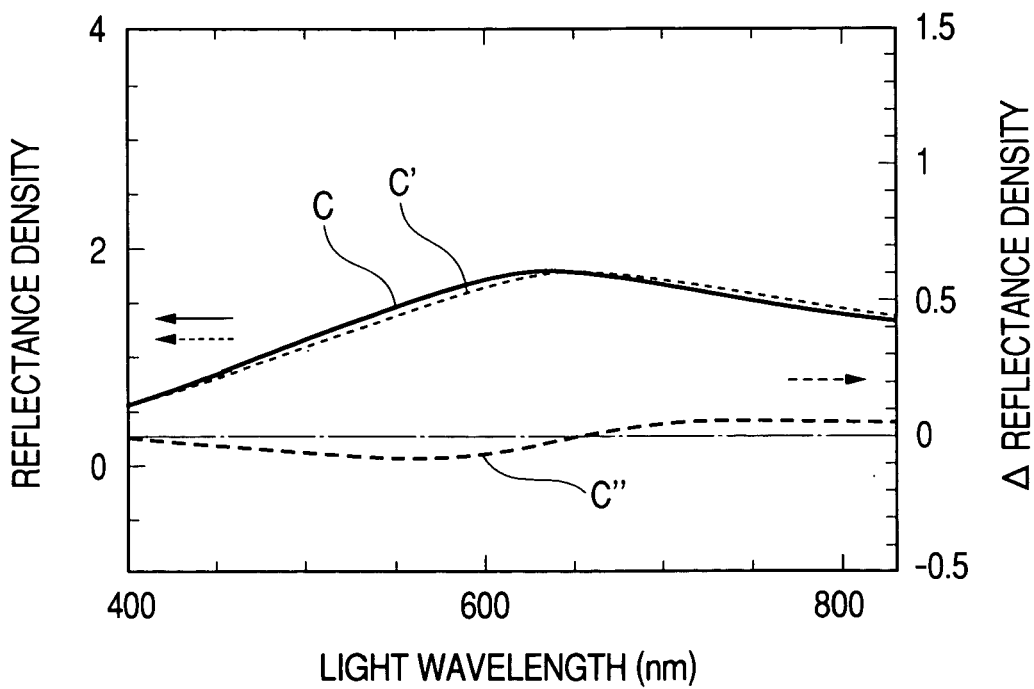
FIG. 8 is a graph showing the change of reflection spectrum before bonding and after bonding with protein.

Computer simulation identical with that in Example 1 was conducted. The model is different from that of Example 1 only in that the refractive index of the optical thin film 13 in FIG. 6 was changed to 2.0 and the thickness was changed to 75 nm. FIG. 8 shows the reflection spectra and specifically the reflectance density spectra at wavelength of 400 nm to 830 nm. The graph shows a reflection spectrum of a sensor applied with the first biochemical substance layer in FIG. 6A as a solid line C, and shows a reflection spectrum after binding of the second biochemical substance in FIG. 6B as a short dashed line C', respectively. Broken line C" shows a differential spectrum formed by subtracting the solid line C from the short dashed line C'. In comparison with FIG. 7 of Example 1, while the peak value for the reflectance density and the peak value for the differential spectrum are decreased, since the reflection spectrum changes by the binding of the second biochemical substance, it can be used as the sensor. As described above, a biochemical sensor chip having higher alkali resistance may be obtained by using an optical thin film of silicon nitride 3 with refractive index of 2.0.

Third Exemplary Embodiment "Example 3"

As described in Example 2, among the silicon nitride films, a film with a refractive index being controlled to 2.0 has desirable alkali resistance. Accordingly, a silicon nitride film with a refractive index controlled to 2.0 is most suitable for the sensor surface. However, in the case of using a film with a refractive index of 2.0 on the silicon substrate in Example 2, since the reflection of light at the boundary with the silicon substrate increases compared with the reflection of a light at the boundary with an aqueous solution, the light interference in the aqueous solution is weak. Then, a biochemical sensor chip having a reflection spectrum identical with that shown in FIG. 7 of Example 1 and having better alkali resistance can be obtained by depositing a silicon nitride film with a refractive index of about 2.4 to about 40 nm on a silicon substrate and further depositing a silicon nitride film with a refractive index of about 2.0 to about 40 nm thereon.

The biochemical sensor chip can be obtained by the method of manufacturing the biochemical sensor chip in Example 1 except for forming silicon nitride with a refractive index of about 2.4 and a thickness of about 40 nm on the surface and the rear surface of the silicon substrate 3 having a substantially planar surface by a CVD method. Further, silicon nitride is formed with a refractive index of about 2.0 to a thickness of about 40 nm further thereon, instead of forming the optical thin film 6 of silicon nitride ($Si_xN_y$, refractive index 2.2) with a thickness of about 70 nm on the surface and the rear surface of the silicon substrate 5 having substantially a planar surface in FIG. 3A.

Figure 9A:
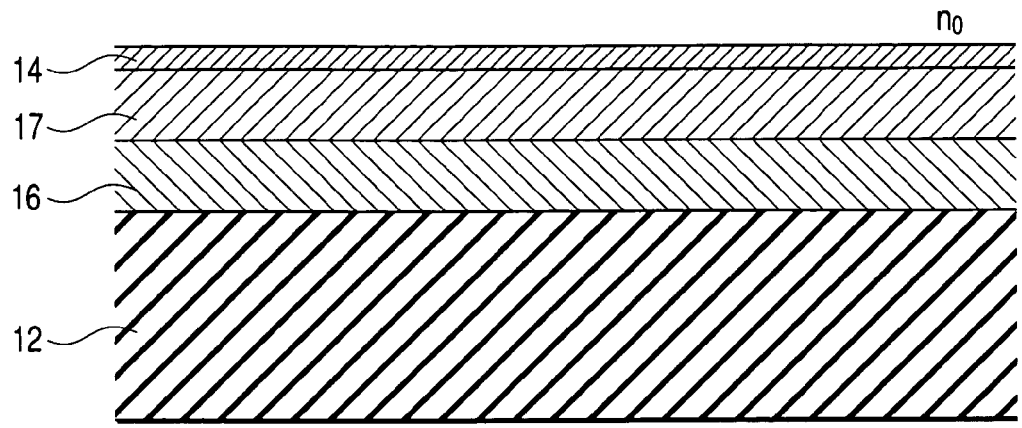
FIG. 9 details two views of the constitution of a biochemical sensor according to the present invention (FIG. 9A and FIG. 9B)
Figure 9B:
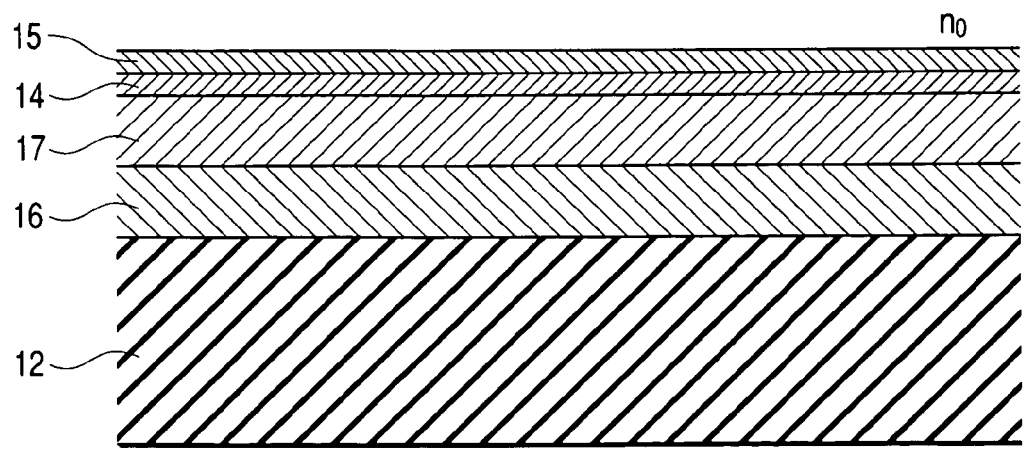

The sensor also shows a distinct interference color in a solution like that in Example 1, and the interference color changes by the binding of a biochemical substance. FIG. 9 shows a model used for computer simulation. The refractive index $n_0$ of the background was 1.3330, and the substrate was silicon. The optical thin film was a dual-layered film (i.e., two layers) comprising a film 16 with a refractive index of 2.4 at a thickness of 40 nm on the silicon substrate and a film 17 with a refractive index of 2.0 at 40 nm thickness. As in Example 1, the first biochemical substance (probe) was a layer 14 with a refractive index of 1.5 and at a thickness of 10 nm (FIG. 9A). By supplying a sample containing the second biochemical substance to the biochemical sensor, the first biochemical substance and the second biochemical substance are binded (FIG. 9B). The second biochemical substance was shown as a layer 15 with a refractive index of 1.5 at a thickness of 10 nm.

Figure 10:
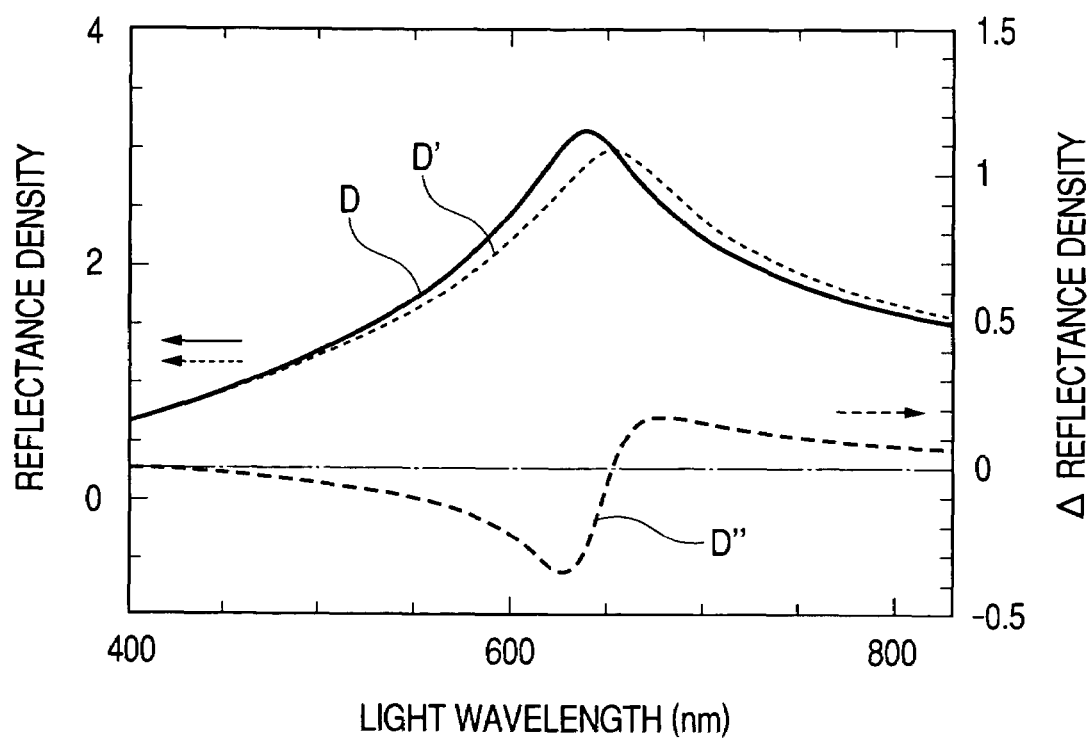
FIG. 10 is a graph showing the change of reflection spectrum before bonding and after bonding with protein.

FIG. 10 shows the reflection spectra and specifically the reflectance density spectra at wavelengths of 400 nm to 830 nm. The graph shows the reflection spectrum of the sensor applied with the first biochemical substance layer in FIG. 9A as a solid line D, and a reflection spectrum after binding of the second biochemical substance in FIG. 9B as a short dashed line D'. A broken line D" is a differential spectrum formed by subtracting the solid line D from the short dahsed line D'. When compared with FIG. 7 for Example 1, it can be seen that the reflection spectrum and the differential spectrum are substantially identical. As described above, a biochemical sensor chip having the same level of performance as the sensor and a high alkali resistance compared with those of Example 1 can be obtained by constituting a dual-layered film in which the silicon nitride film with a refractive index of 2.0 is the uppermost layer of the sensor portion.

In this example, the biochemical sensor chip is obtained by depositing the optical thin film 6 in FIG. 3A according to the manufacturing method of Example 1 as a multi-layered film comprising silicon nitride with a refractive index of about 2.0 and silicon nitride with a refractive index of about 2.4 to about 40 nm thickness and partially fabricating the same as shown in FIG. 3C to form a step. However, the sensor chip can also be obtained by depositing a silicon nitride film with a refractive index of 2.4 at a thickness of about 40 nm at the surface and the rear surface of a substantially planar silicon substrate, forming the same resist pattern as in Example 1 by photolithography, and thereafter etching the silicon nitride film with a refractive index of about 2.4 at a thickness of about 40 nm on the surface of the silicon substrate by using a resist pattern and a mask as a depositing a silicon nitride film with a refractive index of about 2.0 at a thickness of about 40 nm on each of the surface and the rear surface of the substrate. In this case, because not only the sensor portion but the sensor chip surface are entirely covered with silicon nitride with a refractive index of about 2.0 having a high chemical resistance, the chemical resistance may be further improved over previous embodiments.

Fourth Exemplary Embodiment "Example 4"

Figure 11A:
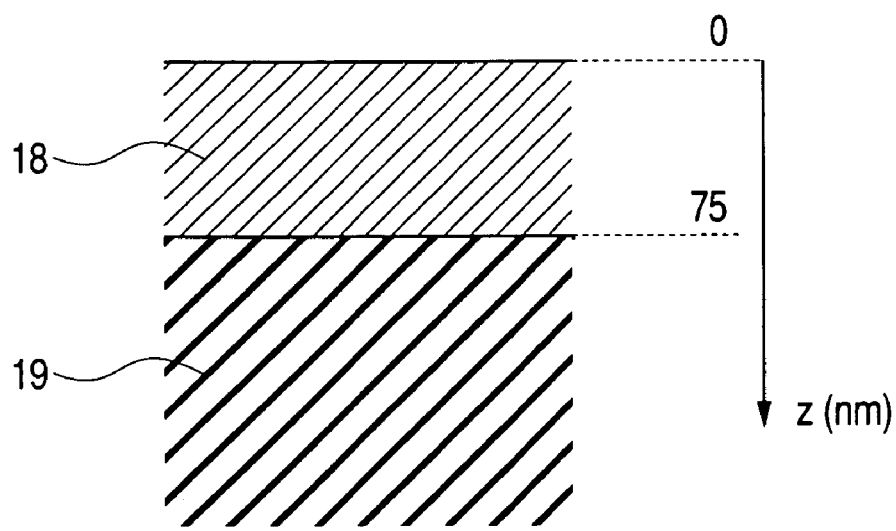
FIG. 11 details two views of the constitution of a biochemical sensor according to the present invention (FIG. 11A and FIG. 11B)
Figure 11B:
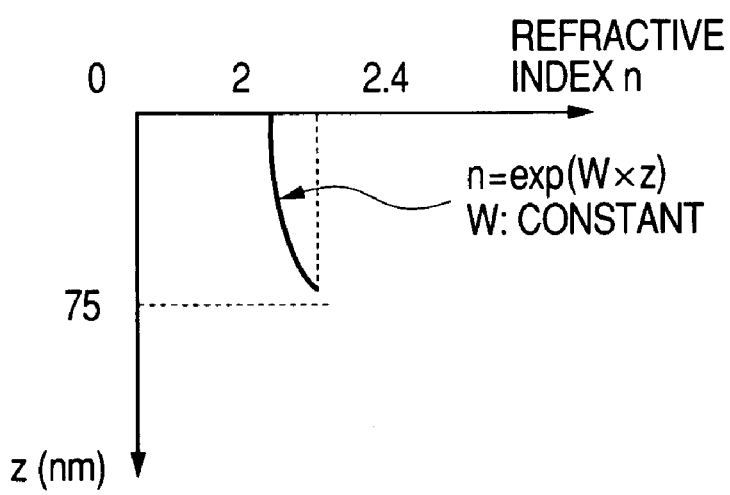

In Example 3, the optical thin film was formed as a dual-layered film comprising two films of different refractive indexes thereby forming the uppermost layer as silicon nitride with a refractive index of 2.0. However, the same effect as in Example 3 can also be obtained by using a gradient-index layer. FIGS. 11A and 11B show an example of a gradient-index layer. As shown in FIG. 11A, the refractive index is changed continuously in an optical thin film 18 at a thickness of about 75 nm. The refractive index is set to about 2.0 at the surface of the sensor and, for a z-axis taken in the direction perpendicular to the optical thin film 18 with the sensor surface being defined as 0, the refractive index is set to about 2.4 on the silicon substrate 19, that is, at Z=75 nm. The refractive index changes in accordance with an exponential function between 0 and 75 nm and refractive index n(z) is defined as: $n(z)=\exp(W \times z)$ as shown in FIG. 11B, in which W represents a constant. In the gradient-index layer, so long as the refractive index at the surface is constant, the change of the refractive index in the inside may be either an exponential change as shown in FIG. 11B or any other continuous change. By setting the refractive index at the surface to about 2.0, the chemical resistance may be improved. Further, an optical thin film suitable to measurement can be formed without forming a plurality of thin films on the silicon substrate.

The biochemical sensor chip can be obtained in the same manner as in Example 1 by forming silicon nitride to a thickness of about 75 nm while controlling the monosilane mixing ratio such that the refractive index changes from 2.4 to 2.0 as shown in FIG. 11 by a CVD method This is instead of forming the optical thin film 6 of silicon nitride ($Si_xN_y$, refractive index 2.2) at a thickness of about 70 nm to each of the surface and the rear surface of the silicon substrate 5 having a substantially planar surface in FIG. 3A. However, a manufacturing method for the biochemical sensor chip in Example 1 by a CVD method may be utilized in this embodiment too.

Figure 12A:
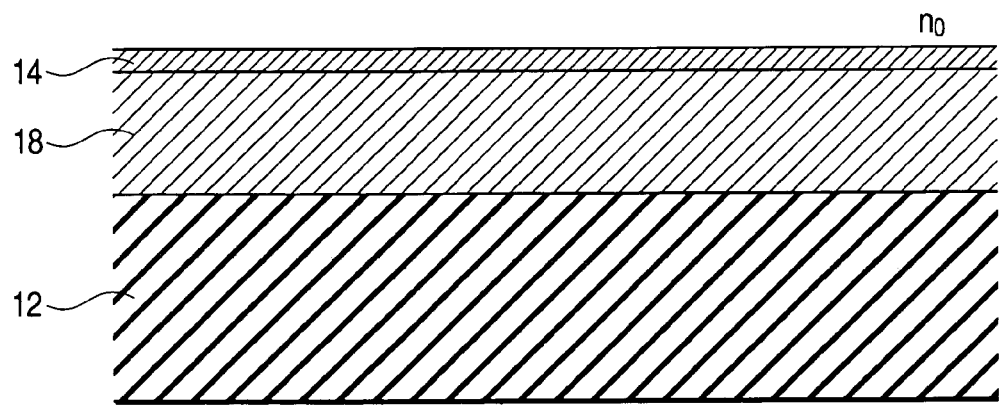
FIG. 12 details two views of the constitution of a biochemical sensor according to the present invention (FIG. 12A and FIG. 12B)
Figure 12B:
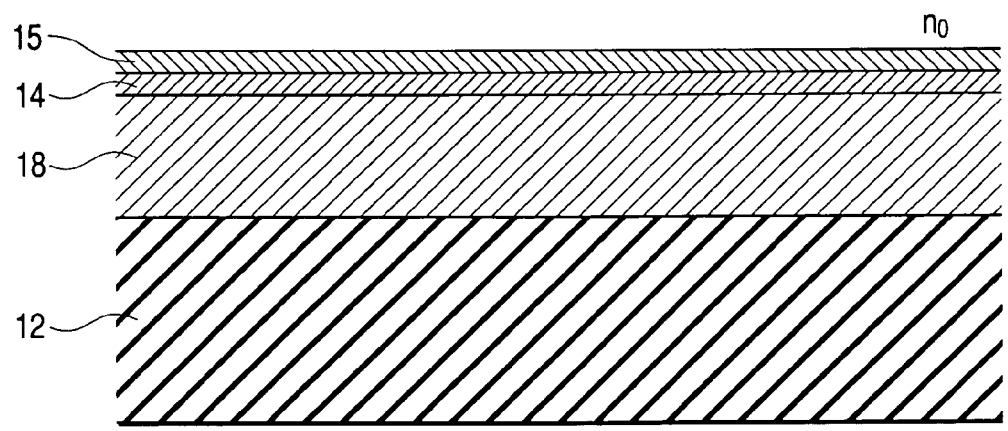

Additionally, the sensor shows a distinct interference color in the solution like in Example 1 and Example 3, and the interference color thereof changes by the binding of a biochemical substance. FIG. 12 shows a model used for computer simulation. The background refractive index no was 1.3330 and the substrate 12 was silicon. The optical thin film was a gradient-index layer 18 with the refractive index being changed from 2.4 to 2.0 shown in FIG. 11. As in Example 1, the first biochemical substance (probe) was a layer 14 with a refractive index of 1.5 at a thickness of 10 nm (FIG. 12A). By supplying a sample containing a second biochemical substance to the biochemical sensor, the first chemical substance and the second biochemical substance are binded (FIG. 12B). The second biochemical substance is shown as a layer 15 with a refractive index of 1.5 at a thickness of 10 nm.

Figure 13:
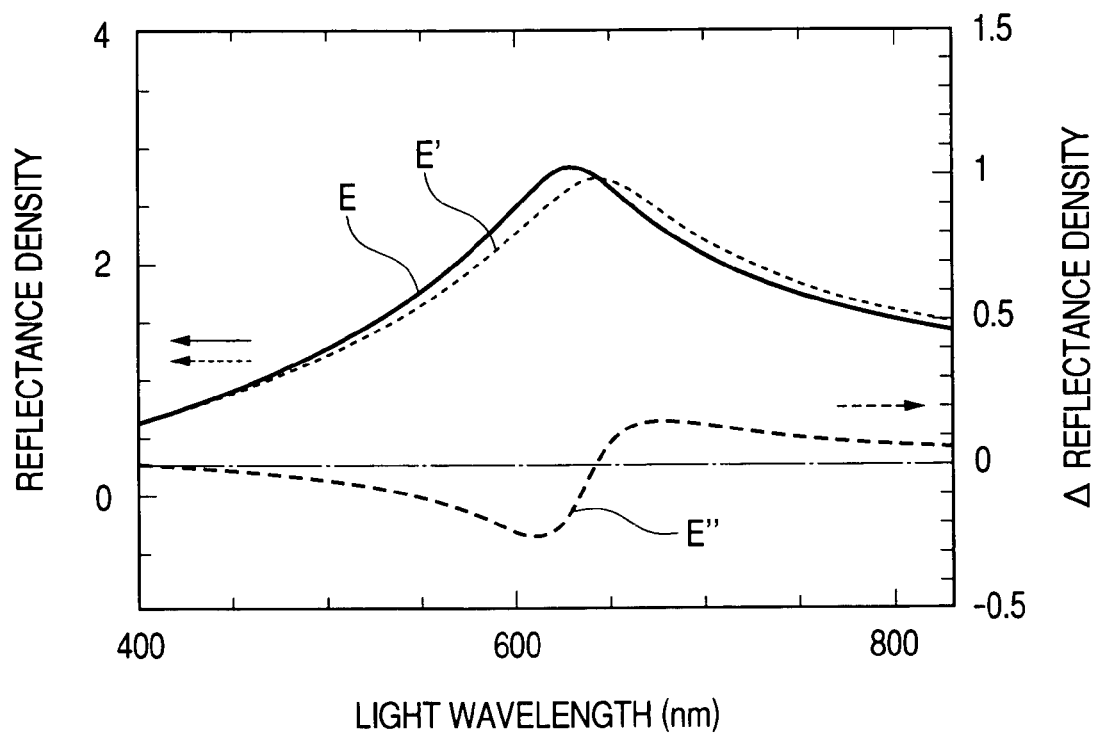
FIG. 13 is a graph showing the change of reflection spectrum before bonding and after bonding with protein.

FIG. 13 shows the reflection spectra and specifically the reflectance density spectra at wavelengths of 400 nm to 830 nm. The graph shows a reflection spectrum of the sensor applied with the first biochemical substance layer in FIG. 12A as a solid line E and a reflection spectrum after binding of the second biochemical substance in FIG. 12B as a short dashed line E'. A broken line E" shows a differential spectrum formed by subtracting the solid line E from the short dashed line E'. It can be seen that the reflection spectrum and the differential spectrum are substantially identical with those in FIG. 7 of Example 1. As described above, a biochemical sensor chip having a performance about at the same level as that of Example 1 and having higher alkali resistance as the sensor can be obtained by forming on the sensor surface with a gradient-index layer using silicon nitride with a refractive index of 2.0.

Also in this example, a silicon nitride film with a refractive index of about 2.0 may be deposited from about 0.5 nm to about 10 nm for the surface fabricated with the gradient-index layer for improving the chemical resistance of the entire chip surface in addition to the sensor surface. In this case, the film thickness and the gradient-index are determined by considering both the gradient-index layer and the silicon film with a refractive index of about 2.0 to be deposited subsequently.

Fifth Exemplary Embodiment "Example 5"

Figure 14:
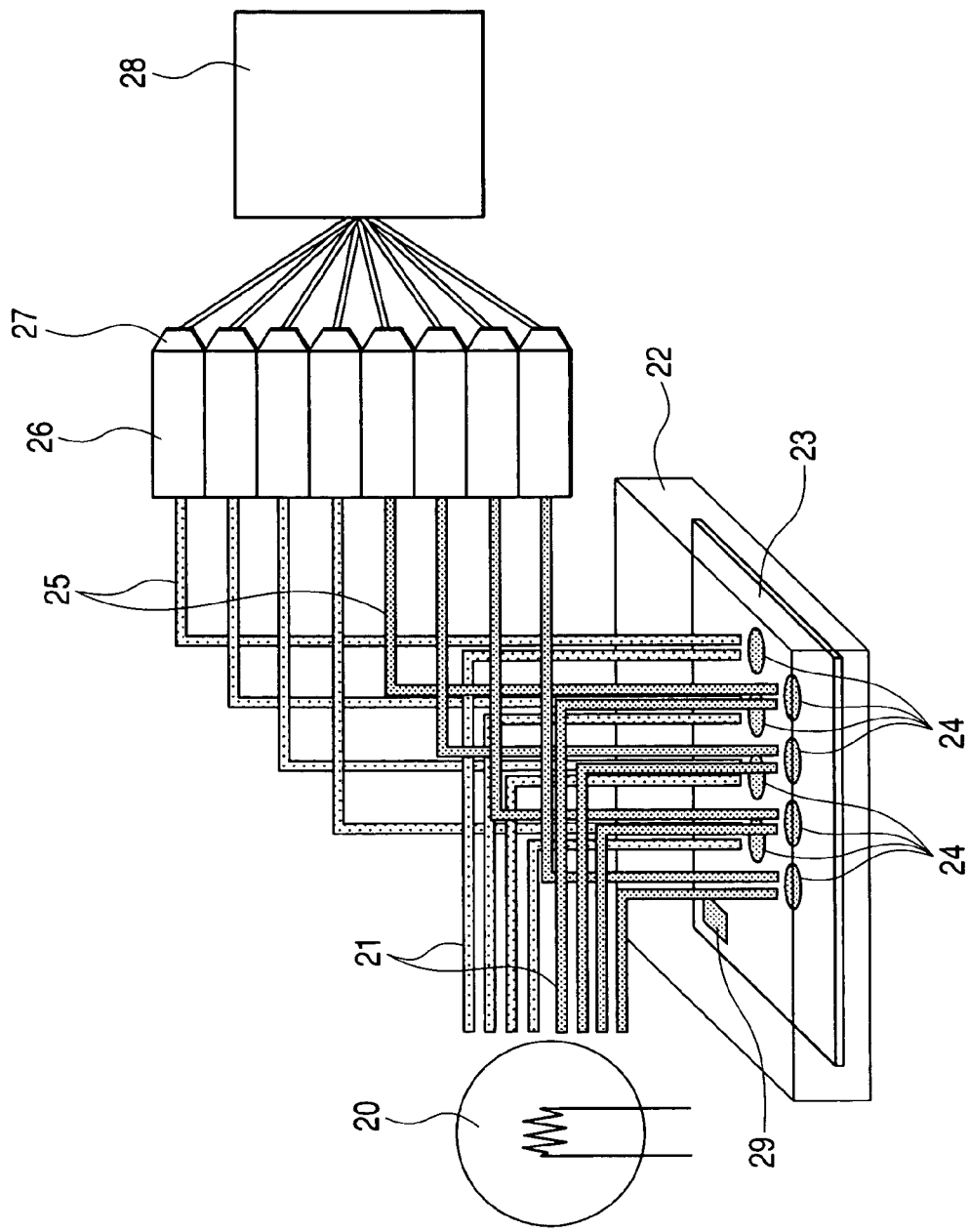
FIG. 14 is a block diagram showing a detection apparatus according to the present invention.
Figure 15:
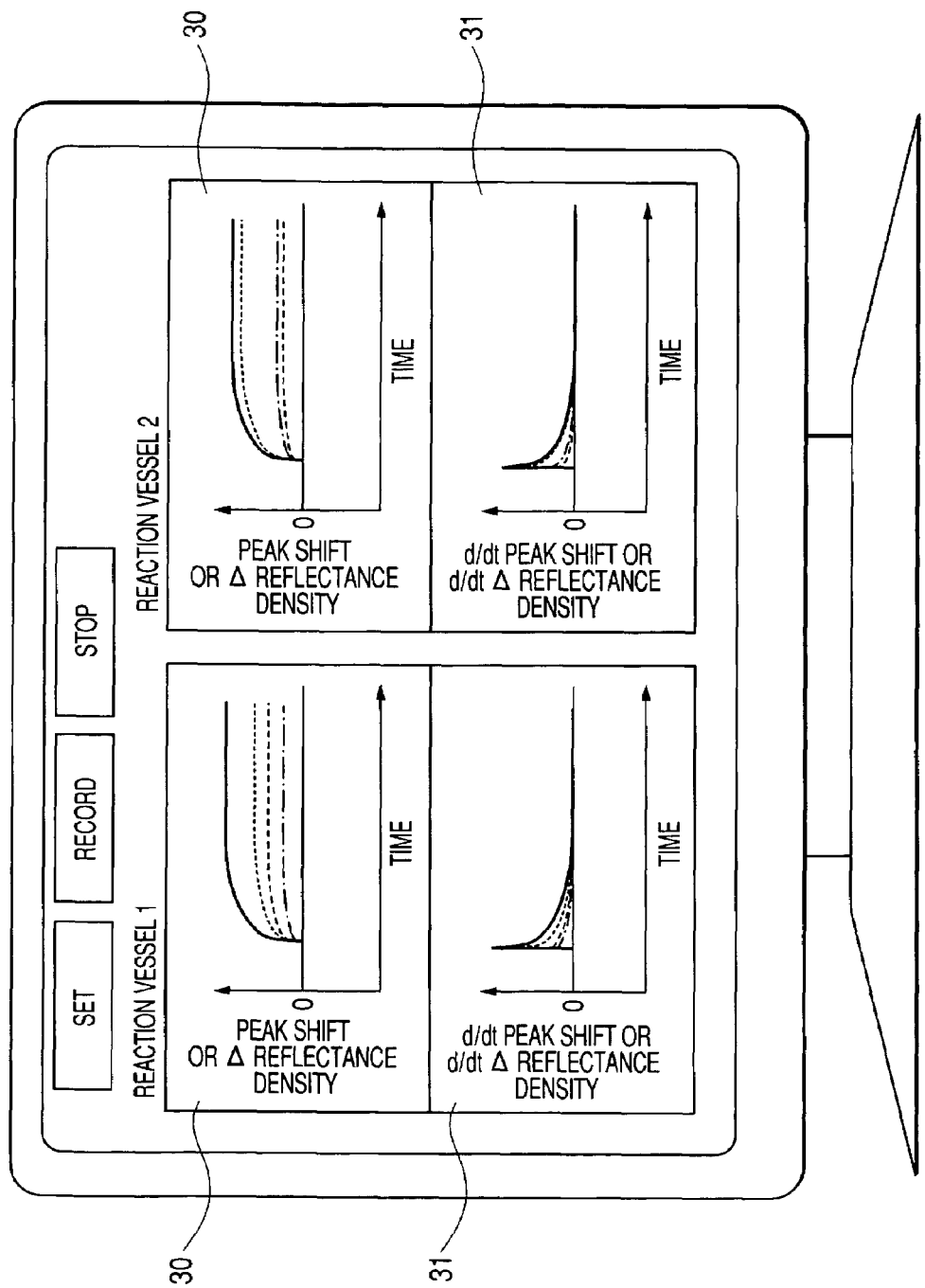
FIG. 15 is a view showing a display screen of a computer in a detection apparatus.
Figure 16:
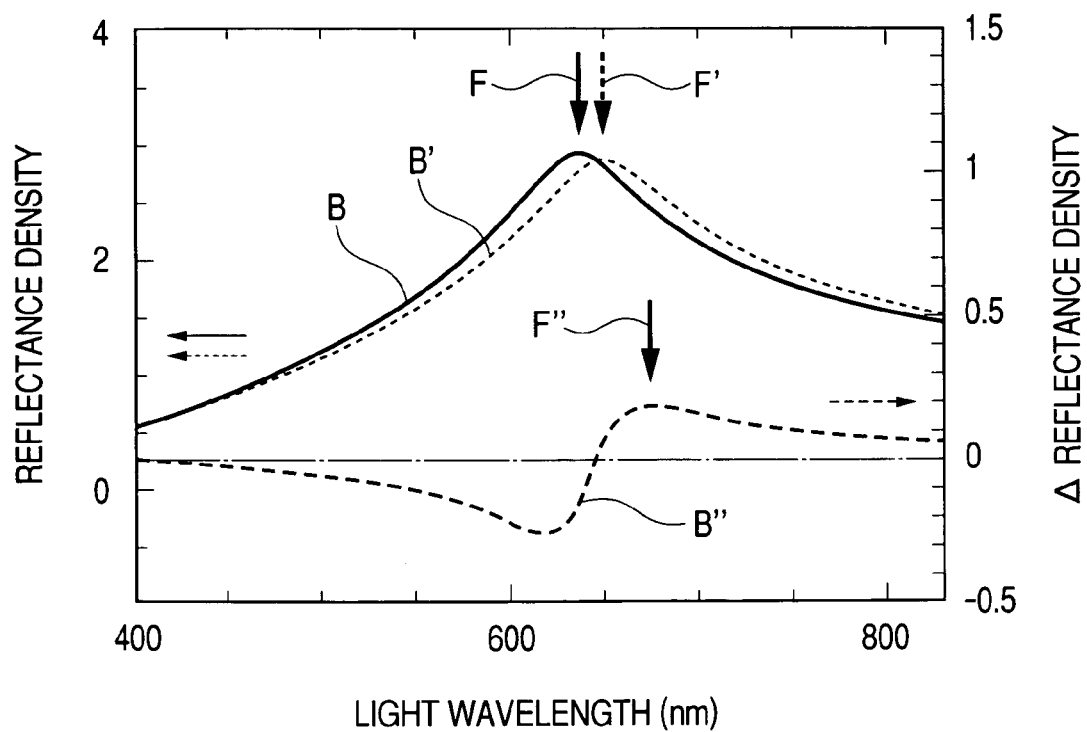
FIG. 16 is a graph showing the change of reflection spectrum before bonding and after bonding with protein.
Figure 17:
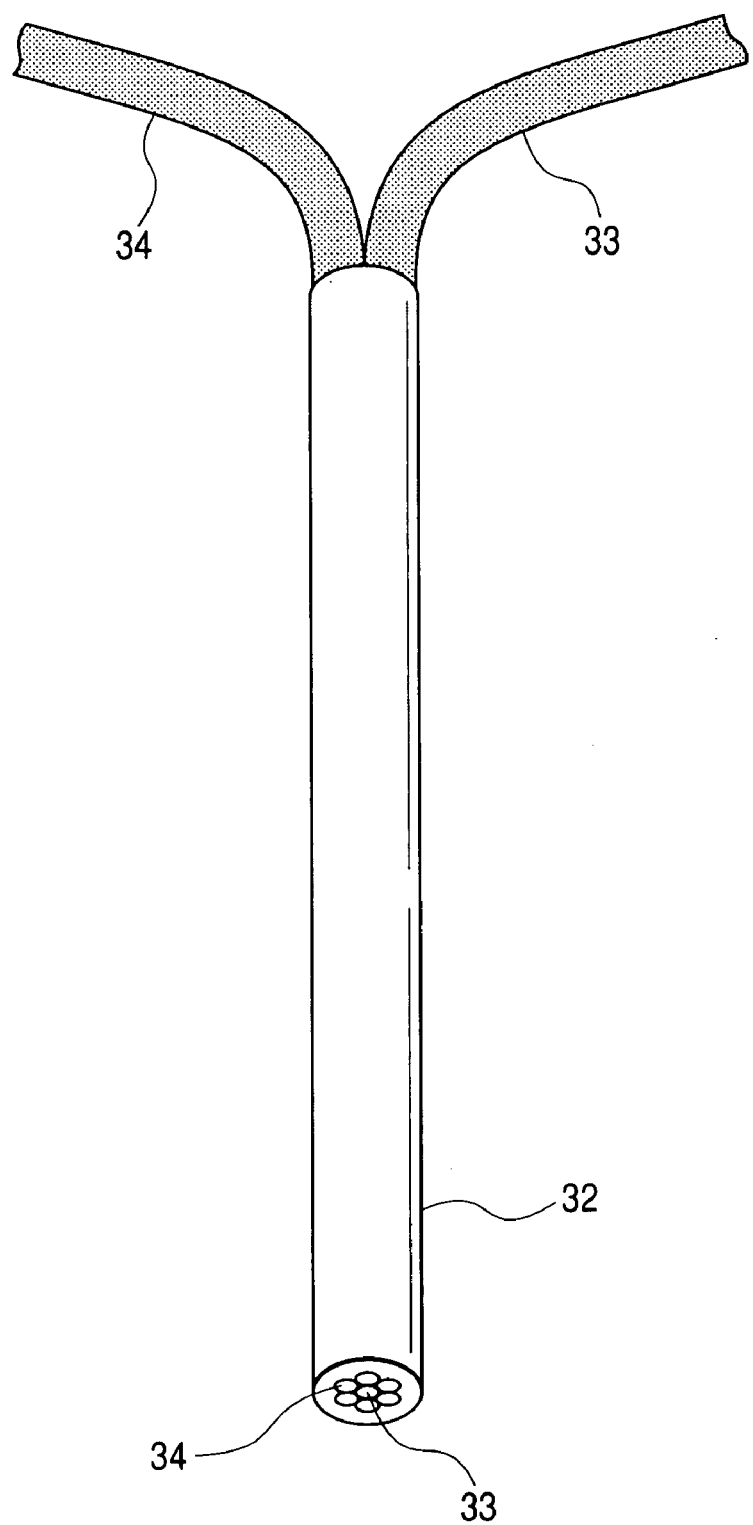
FIG. 17 is a perspective view showing the optical system in a detection apparatus.
Figure 18:
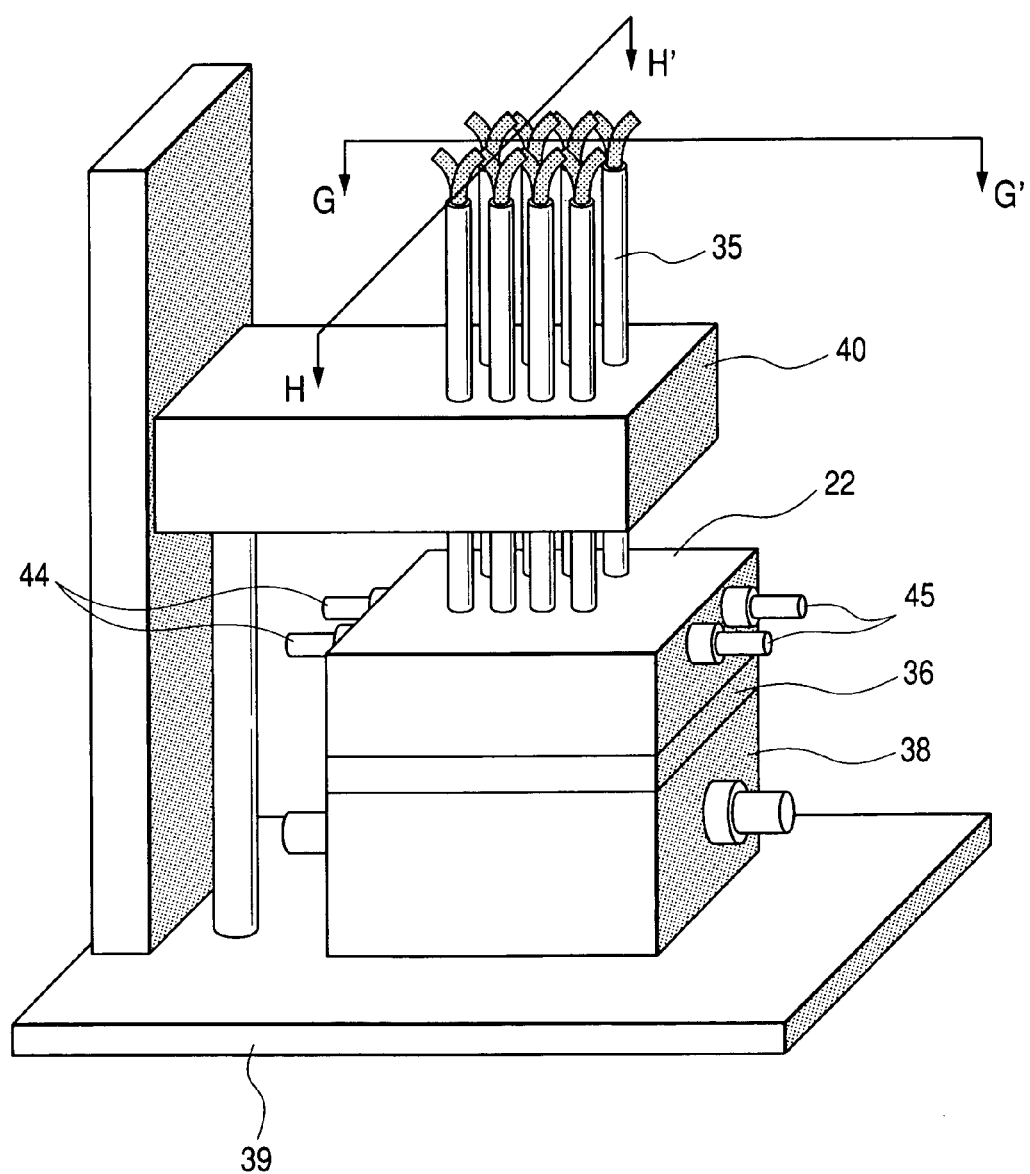
FIG. 18 is a perspective view showing the reaction vessel in a detection apparatus.
Figure 19:
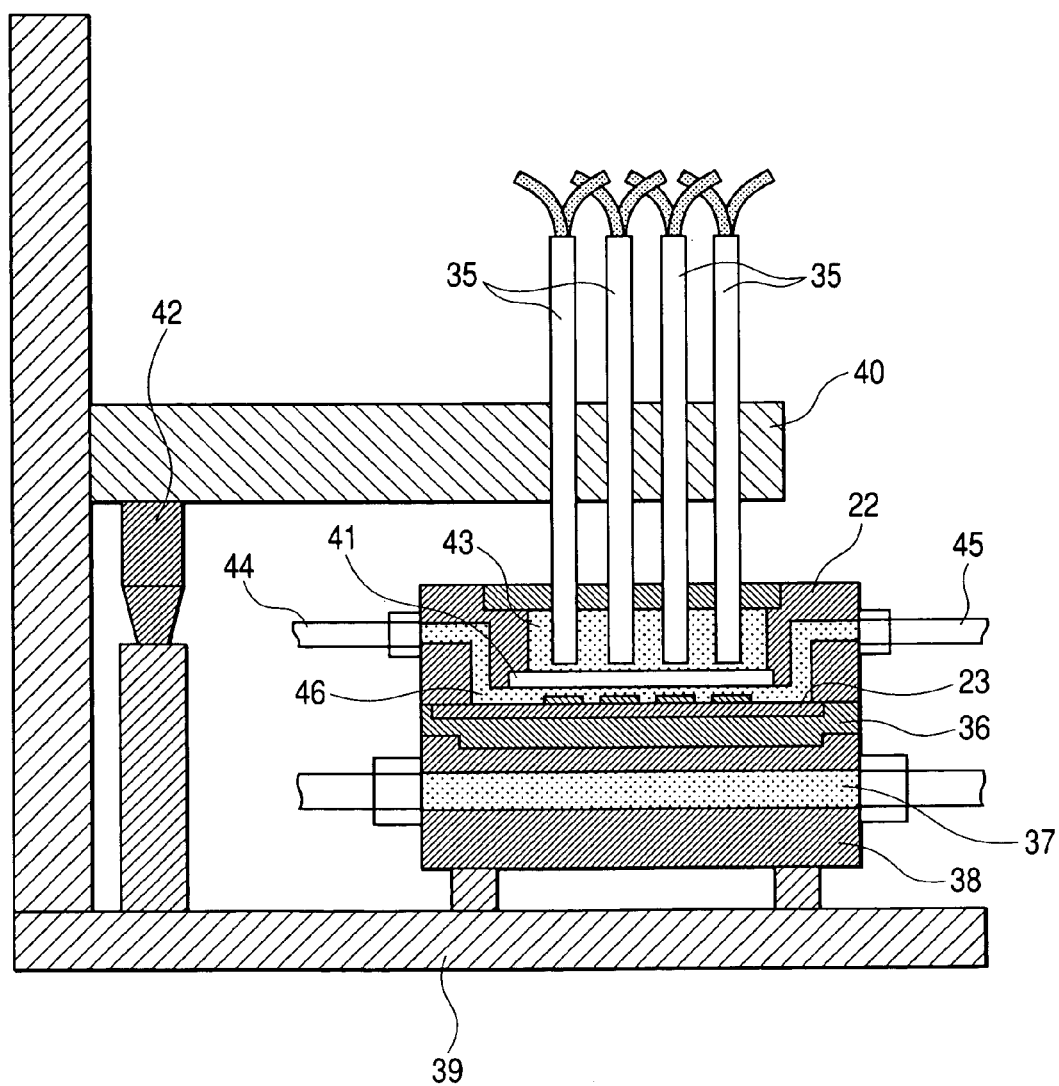
FIG. 19 is a cross sectional view taken along line G-G' in FIG. 18.
Figure 20:
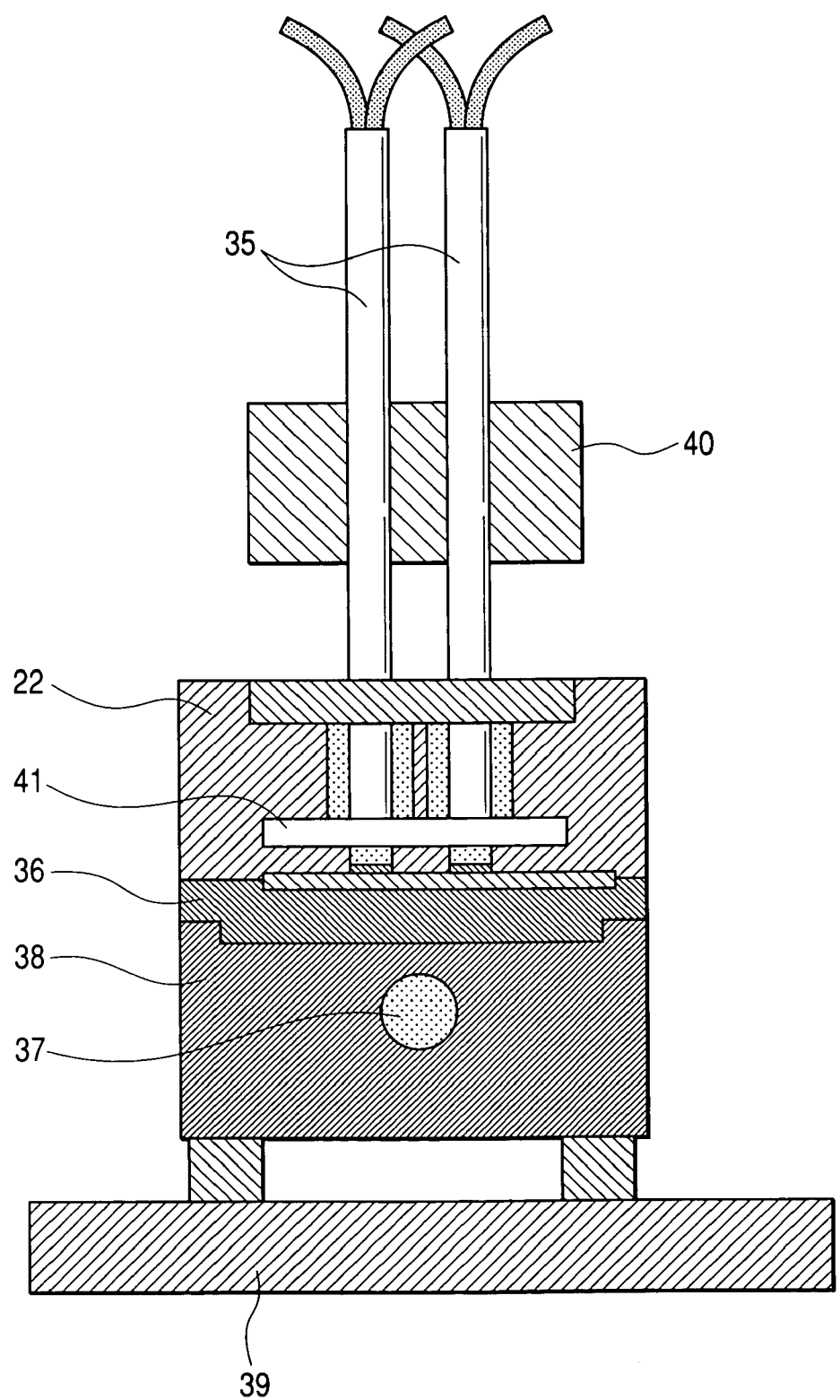
FIG. 20 is a cross sectional view taken along line H-H' in FIG. 18.

An apparatus for real time detection of the change of the interference color of the optical thin film sensor in a solution according to the present invention is now described with reference to the figures. FIG. 14 is a block diagram showing an example of the invention, FIG. 15 is a view showing an example for the display screen of a computer in a detection apparatus, FIG. 16 is a graph showing an amount detected by the detection apparatus, and FIG. 17 is a perspective view showing an example of an optical system in the detection apparatus. FIG. 18 shows a perspective view of an exemplary reaction cell in the detection apparatus according to the invention. FIGS. 19 and 20 are cross sectional views taken along lines G-G' and H-H' in FIG. 18, respectively.

In the detection apparatus according to the present invention, as shown in FIG. 14, a light from a white light source 20 such as a tungsten lamp is irradiated by way of an irradiation optical system 21. The optical system 21 comprises optical fibers leading to a plurality of optical thin film sensor portions 24 (described in Example 1 to Example 4) on a sensor chip 23 placed in the reaction cell 22. A reflected light from the optical thin film sensor portion 24 is transmitted by way of a light collecting optical system 25 and is measured in real time by a plurality of spectrometers 26 and a multi-channel photoreceiver 27 such as a plurality of CCDs or photodiode array. The data is taken as reflection spectra and is sent into a computer 28. The computer 28 calculates in real time the change of the peak position for the reflectance density or the change of the reflectance density at a single wavelength for the reflection spectrum in each of the optical thin film sensor portions 24 described in Examples 1 to 4. The computer preferably plots the change over time in real time as a graph 30 on the display of FIG. 15 and records the same.

FIG. 16 shows the peak position for the reflectance density and the wavelength position for the change of the reflectance density at a single wavelength by arrows F, F', F" using the graph for the solid line B, short dahsed line B' and broken line B" in FIG. 7 of Example 1. The amount of the change of the peak position of the reflectance density shows the amount of change of the peak position from the position of arrow F to the position of arrow F'. The wavelength position for the change of the reflectance density at a single wavelength is preferably a wavelength position as shown by the arrow F" with a large value for the differential spectrum. Time differentiation in graph 30 is displayed on graph 31 and recorded (see FIG. 15). This can facilitate observation of the start and saturation of binding. By conducting measurements in real time in the specimen solution, the reaction can be examined more rapidly and precisely compared with the case of measuring the sensor chip by taking it out into the air.

FIG. 17 shows an example of the irradiation optical system 21 using optical fibers and a collecting optical system 25. As shown in FIG. 17, an optical fiber bundle in which seven glass optical fibers each of 200 μm diameter are packed into a metal pipe 32 of 1.5 mm diameter. The opposite end of the optical fiber 33 situated at the center of the optical fiber bundle is placed before the slit of the photospectrometer 26. Opposite ends of remaining six optical fibers 34 surrounding the optical fibers 33 situated at the center are placed before the white light source 20.

FIG. 18, FIG. 19, and FIG. 20 show an example of a detection apparatus using the optical fiber bundle 35 shown in FIG. 17. As shown in FIGS. 18, 19, and 20, the optical fiber bundles 35 are fixed to a movable stand 40 attached to a table 39 on which a reaction cell 22, a sensor chip holder 36 for placing the sensor chip at a predetermined position, and a cooler/heater 38 for temperature control by circulating cooling water or warming water 37 are fixed and placed just above the optical thin film sensor portion 24. As described above, light is irradiated from each of the optical fiber bundles 35 through a substantially transparent optical window 41 to each of the optical thin film sensor portions 24 situated just below.

When the sensor chip 23 is mounted to the sensor chip holder 36, it can be mounted in an appropriate direction by the aid of a mark 29 showing the direction of the sensor chip. Further, when the sensors are arranged such that they are not in rotational symmetry (see FIG. 5, no symmetry when rotated about a central axis), that is, they are asymmetric with respect to the rotating direction of the sensor chip, error with respect to the mounting direction in a case where the sensor chip is mounted in an erroneous direction can be judged by the detector based on the difference of the reflection intensity. In connection with this, the optical fiber bundle 35 is made such that the arrangement for the ends facing the sensor chip is not in rotational symmetry, that is, asymmetrical with respect to the rotational direction (into and out of FIG. 19). Thus, appropriate measurements can be conducted with respect to the sensor chip.

The movable stand 40 also includes an optical fiber holding portion for holding the optical fiber bundle. A positioning mechanism 42 for defining the position of the movable stand is attached such that the position of the optical fiber bundle 35 relative to the optical thin film sensor portion 22 is reproduced. Generally, the interference color of the optical thin film depends on the incident angle and the reflection angle of the light used for the measurement. By reproducing the position for the optical fiber bundle 35 utilizing the positioning mechanism 42, the angle of the light irradiated from the optical fiber bundle 34 for the irradiation optical system 21 and the angle for the light reflected at the optical thin film sensor portion 24 and collected by the optical fibers 33 of the collecting optical system 25 are reproduced. It is desirable that the angle is determined within the range of the light irradiation angle and the light collection angle, which are determined based upon the numerical aperature of the optical fibers that are used. Further, by the use of the positioning mechanism 42, damage caused by collision of the optical fiber bundle 35 to the optical window 41 can be avoided.

In this apparatus, by bringing the optical fiber bundle and the optical window 41 significantly close to each other, the effect of the reflection of the light at the optical window 41 on the measurement for the reflection spectrum can be reduced. Examination of the binding of various kinds of biochemical substances at one time can be enabled by increasing the number of the optical thin film sensor portions 24 and the optical fiber bundles 35. A space 43 for containing a liquid is disposed between the top ends of the optical fiber bundles 35 and the optical window 41. This can reduce the reflection of light at the boundary between the top end of the optical fiber bundle 35 and the optical window 41 to decrease the effect on the measurement of the reflection spectrum. Further, while droplets or frost may sometimes be deposited at the periphery of the reaction cell 22 during cooling, containment of the liquid in the space 43 can prevent the effects due to the deposition of water droplets or frost on the measurement of the reflection spectrum.

Further, binding and dissociation between the biochemical substances can be detected in real time, by allowing a sample solution 46 containing the biochemical substance to flow from the solution inlet 44 to the solution exit 45 by using, for example, liquid delivery pumps and sample injectors to feed the sample solution 46 to two reaction cells 22 independent of each other. This process establishes a state in which the sample solution 46 containing the biochemical substance passes through the gap between the optical window 41 and each of the optical thin film sensor portions 24 for a certain period of time.

Sample solutions 46 which are different from each other can be injected to the independent two reaction cells 22. The solution inlet 44 and the solution exit 45 are located above the reaction vessel and discharge of bubbles can be promoted when they intrude into or are generated from the reaction cell 22. Generally, binding between biochemical substances depends on the circumstantial temperature. By controlling the temperature of the reaction cell 22 by the cooler-heater 38, the temperature dependence of the binding of chemical substance to be measured may be examined. In this case, for improving the heat conductivity to the sensor chip 23, the sensor chip holder 36 and the cooler-heater 38 is made partially or entirely of a metal. The cooler-heater 38 may also be a Peltie device.

An example of the procedures of liquid delivery and measurement is detailed below. In the initial stage, a buffer solution not containing a sample is delivered. Then, a sample solution is delivered for a predetermined period of time to examine the binding of the second biochemical substance to the first biochemical substance. Successively, a buffer solution not containing the sample is delivered for a certain period of time. In this case, dissociation of the second biochemical substance from the first biochemical substance is examined. Then, 20 mM of hydrochloric acid is delivered for 3 min to dissociate the second biochemical substance binded to the first biochemical substance. Subsequently, a buffer solution not containing the sample is delivered and the process is returned to the initial stage. In this example, since a plurality of specimens can be detected substantially simultaneously in real time, binding between the biochemical substances can be measured at a higher throughput.

The sensor and the measuring apparatus according to the present invention are used for the measurement of binding between substances, particularly, between biochemical substances. Specifically, they can be utilized for the analysis of the interaction between molecules for the research of medicinal substances in drug discovery, for the screening of pathogenesis in medical and inspection organs and for use as laboratory instruments.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. A chip comprising;
    a silicon substrate having a first surface and a rear surface;
    a first silicon nitride film disposed on the first surface of the silicon substrate; and
    a second silicon nitride film disposed on the rear surface of the silicon substrate, wherein the first silicon nitride film has a first region for immobilizing a probe for binding a biochemical substance to the probe.

2. A chip according to claim 1, wherein the first region has a thickness larger than other regions of the first silicon nitride film.

3. A chip according to claim 1, wherein the refractive index of the first silicon nitride film is within a range of value from about 2.0 to about 2.6.

4. A chip according to claim 1, wherein the compositional ratio x/y between silicon and nitrogen in the first silicon nitride film is no more than 1.1, in which x represents the amount of silicon and y represents the amount of nitrogen.

5. A chip according to claim 1, further comprising:
    a probe immobilized in said first region of said first silicon nitride film, wherein the probe is formed of protein.

6. A chip according to claim 1, wherein the probe is formed of protein.

7. A chip according to claim 1, wherein the first region of said first silicon nitride film has a refractive index of about 2.2.

8. A chip according to claim 1, wherein the first region of said first silicon nitride film has a refractive index of about 2.0.

9. A chip according to claim 1, wherein said first silicon nitride film is comprised of a third and a fourth silicon nitride film, and further wherein said third silicon nitride film is disposed on the surface of the silicon substrate and has a refractive index of about 2.4 and said fourth silicon nitride film disposed on the surface of the third silicon nitride film and has a refractive index of about 2.0.

10. A chip according to claim 9, wherein said second silicon nitride film is comprised of a fifth and a sixth silicon nitride film, and further wherein said fifth silicon nitride film is disposed on the surface of the silicon substrate and has a refractive index of about 2.4 and said sixth silicon nitride film disposed on the surface of the fifth silicon nitride film and has a refractive index of about 2.0.

11. A chip according to claim 1, wherein each of the first silicon nitride film and the second silicon nitride film has a refractive index of about 2.4 at a surface in contact with the silicon substrate and a refractive index of about 2.0 at an opposite surface, further wherein the refractive index changes continuously from the surface in contact with the silicon substrate to the opposite surface.

12. A chip according to claim 1, wherein each of the first silicon nitride film and the second silicon nitride film has a surface in contact with the silicon substrate and an opposite surface and has a refractive index that changes exponentially from the opposite surface to the surface in contact with the silicon substrate.

13. A chip according to claim 11, further comprising:
a third silicon nitride film having a thickness of about 0.5 nm to about 10 nm and having a refractive index of about 2.0 disposed on said first silicon nitride film; and
a fourth silicon nitride film having a thickness of about 0.5 nm to about 10 nm and having a refractive index of about 2.0 disposed on said second silicon nitride film.

14. A chip according to claim 12, further comprising:
a third silicon nitride film having a thickness of about 0.5 nm to about 10 nm and having a refractive index of about 2.0 disposed on said first silicon nitride film; and
a fourth silicon nitride film having a thickness of about 0.5 nm to about 10 nm and having a refractive index of about 2.0 disposed on said second silicon nitride film.

* * * * *